US009609887B2

(12) United States Patent
Quinlan et al.

(10) Patent No.: US 9,609,887 B2
(45) Date of Patent: Apr. 4, 2017

(54) SWEETENER COMPOSITIONS CONTAINING MONK FRUIT EXTRACT AND REBAUDIOSIDES A AND B

(71) Applicant: Tate & Lyle Ingredients Americas LLC, Hoffman Estates, IL (US)

(72) Inventors: Mary Elizabeth Quinlan, Reading (GB); Yuqing Zhou, Mt. Zion, IL (US)

(73) Assignee: TATE & LYLE INGREDIENTS AMERICAS LLC, Hoffman Estates, IL (US)

( * ) Notice: Subject to any disclaimer, the term of this patent is extended or adjusted under 35 U.S.C. 154(b) by 0 days.

(21) Appl. No.: 13/956,996

(22) Filed: Aug. 1, 2013

(65) Prior Publication Data

US 2014/0037814 A1    Feb. 6, 2014

Related U.S. Application Data

(60) Provisional application No. 61/678,273, filed on Aug. 1, 2012.

(51) Int. Cl.
| | |
|---|---|
| *A23L 1/221* | (2006.01) |
| *A23L 2/60* | (2006.01) |
| *A61K 36/42* | (2006.01) |
| *A23L 27/30* | (2016.01) |

(52) U.S. Cl.
CPC .............. *A23L 1/221* (2013.01); *A23L 2/60* (2013.01); *A23L 27/36* (2016.08); *A61K 36/42* (2013.01); *A23V 2200/00* (2013.01)

(58) Field of Classification Search
CPC .................................. A23L 1/221; A23L 2/56
USPC ......................................................... 426/548
See application file for complete search history.

(56) References Cited

U.S. PATENT DOCUMENTS

| | | | |
|---|---|---|---|
| RE30,820 E | 12/1981 | Walon | |
| 4,361,697 A | 11/1982 | Dobberstein | |
| 4,612,942 A | 9/1986 | Dobberstein | |
| 5,411,755 A | 5/1995 | Downton | |
| 5,433,965 A | 7/1995 | Fischer | |
| 5,690,725 A | 11/1997 | Tucker | |
| 6,335,461 B1 | 1/2002 | Amino | |
| 7,575,772 B2 | 8/2009 | Shi | |
| 7,815,956 B2 | 10/2010 | Lee | |
| 7,884,265 B2 | 2/2011 | Morita | |
| 8,017,168 B2 | 9/2011 | Prakash | |
| 8,962,698 B2 | 2/2015 | Bridges | |
| 9,024,012 B2 | 5/2015 | Erickson | |
| 9,044,038 B2 | 6/2015 | Yoshinaka | |
| 9,155,166 B2 | 10/2015 | Chobot | |
| 2005/0152997 A1 | 7/2005 | Selzer | |
| 2006/0003053 A1 | 1/2006 | Ekanayake | |
| 2007/0116823 A1 | 5/2007 | Prakash | |
| 2007/0116825 A1 | 5/2007 | Prakash | |
| 2007/0116828 A1* | 5/2007 | Prakash et al. | 426/548 |
| 2007/0116836 A1 | 5/2007 | Prakash | |
| 2007/0116839 A1 | 5/2007 | Prakash | |
| 2007/0116840 A1 | 5/2007 | Prakash | |
| 2007/0224292 A1 | 9/2007 | Brunner | |
| 2008/0107775 A1 | 5/2008 | Prakash et al. | |
| 2008/0226788 A1 | 9/2008 | Chang | |
| 2008/0226796 A1 | 9/2008 | Lee et al. | |
| 2008/0226802 A1 | 9/2008 | Lee | |
| 2008/0274258 A1 | 11/2008 | Shi | |
| 2008/0292775 A1 | 11/2008 | Prakash | |
| 2008/0299277 A1* | 12/2008 | Chao et al. | 426/548 |
| 2009/0162487 A1 | 6/2009 | Bell et al. | |
| 2009/0196966 A1 | 8/2009 | West | |
| 2010/0099857 A1 | 4/2010 | Evans | |
| 2010/0112154 A1 | 5/2010 | Abelyan | |
| 2010/0267847 A1 | 10/2010 | Yoshinaka et al. | |
| 2010/0285195 A1 | 11/2010 | Fisher | |
| 2010/0316782 A1 | 12/2010 | Shi | |
| 2011/0021456 A1 | 1/2011 | Lyndon | |
| 2011/0023192 A1 | 1/2011 | Morita | |
| 2011/0038957 A1 | 2/2011 | Fowler | |
| 2011/0052755 A1 | 3/2011 | Fiorenza et al. | |
| 2011/0160311 A1* | 6/2011 | Prakash | A23L 1/09 514/777 |
| 2011/0287164 A1 | 11/2011 | Markosyan | |
| 2012/0059071 A1 | 3/2012 | Markosyan | |
| 2012/0183648 A1* | 7/2012 | Sun | A23L 1/22 426/72 |
| 2012/0264831 A1 | 10/2012 | Bridges et al. | |

(Continued)

FOREIGN PATENT DOCUMENTS

| | | |
|---|---|---|
| CN | 1094892 | 11/1994 |
| CN | 101062077 | 10/2007 |

(Continued)

OTHER PUBLICATIONS

International Search Report and Written Opinion Issued for International Application No. PCT/US2013/052821, Mailed Oct. 30, 2013.
UKIPO Combined Search and Examination Report Issued for Application No. GB1217700.2 dated Jan. 29, 2013.
"Layn's Luo Han Guo Natural Sweetener has acheived GRAS status", Lovia, Taking Stevia to the Next level, Layn Natural Ingredients, http://www.layncorp.com/news.php (May 1, 2011), 1 pg.
"Lovia", Layn Natural Ingredients, http://www.layncorp.com/showproducts.php?id=126, accessed on Jan. 20, 2012, 2 pgs.
Chinese Office Action mailed Jul. 1, 2014 in related Application No. 201180069627.7.
Compounds (C26H30O10) provided by Chemspider (http://www.chemspider.com/Search.aspx?rid=5a954e4d-a6f4-41f8-b7d0-1b2e5cea4bba), downloaded on Apr. 2, 2013.

(Continued)

*Primary Examiner* — Jill Warden
*Assistant Examiner* — Bhaskar Mukhopadhyay
(74) *Attorney, Agent, or Firm* — RatnerPrestia

(57) ABSTRACT

Sweetener compositions useful as non-caloric replacements for sugars in food and beverages are provided by combinations of monk fruit extract (containing mogroside V) with rebaudioside A and B, which have improved taste profiles as compared to other non-caloric sweeteners.

11 Claims, No Drawings

(56) References Cited

U.S. PATENT DOCUMENTS

| | | | |
|---|---|---|---|
| 2012/0269954 A1* | 10/2012 | Bridges | A23L 2/60 426/658 |
| 2012/0289687 A1 | 11/2012 | Erickson | |
| 2013/0071537 A1 | 3/2013 | Shi | |
| 2013/0136838 A1 | 5/2013 | San Miguel et al. | |
| 2013/0164420 A1* | 6/2013 | Catani et al. | 426/302 |
| 2013/0309389 A1 | 11/2013 | Carlson | |
| 2014/0234511 A1 | 8/2014 | Hansen | |

FOREIGN PATENT DOCUMENTS

| | | |
|---|---|---|
| CN | 101327244 | 12/2008 |
| CN | 101557726 | 10/2009 |
| CN | 101657112 | 2/2010 |
| CN | 101690573 | 4/2010 |
| CN | 101854814 | 10/2010 |
| CN | 101863946 | 10/2010 |
| CN | 101970450 | 2/2011 |
| CN | 102060892 | 5/2011 |
| CN | 102084982 | 6/2011 |
| CN | 102093445 | 6/2011 |
| CN | 102093447 | 6/2011 |
| CN | 103402374 | 11/2013 |
| EP | 0154235 | 9/1985 |
| EP | 2 215 914 | 8/2010 |
| EP | 2 425 721 | 3/2012 |
| EP | 2486806 | 8/2012 |
| JP | 5283986 | 7/1977 |
| JP | 52083731 | 7/1977 |
| JP | 5312466 | 2/1978 |
| JP | 5871868 | 4/1983 |
| JP | 59120073 | 7/1984 |
| JP | 60199364 | 10/1985 |
| JP | 11046701 | 2/1999 |
| JP | 2000287642 | 10/2000 |
| JP | 2003274911 | 9/2003 |
| JP | 2009517031 | 4/2009 |
| JP | 2010507376 | 3/2010 |
| JP | 2013518118 | 12/2013 |
| JP | 2013545490 | 12/2013 |
| RU | 2160310 | 12/2000 |
| WO | 2006072921 | 7/2006 |
| WO | 2006093229 | 9/2006 |
| WO | 2007061898 | 5/2007 |
| WO | 2008030121 | 3/2008 |
| WO | 2008091547 | 7/2008 |
| WO | WO 2008/112991 | 9/2008 |
| WO | 2009006208 | 1/2009 |
| WO | 2009016374 | 2/2009 |
| WO | 2009063921 | 5/2009 |
| WO | 2009071277 | 6/2009 |
| WO | 2009086049 | 7/2009 |
| WO | 2009093610 | 7/2009 |
| WO | 2009108680 | 9/2009 |
| WO | 2009140394 | 11/2009 |
| WO | 2010038911 | 4/2010 |
| WO | 2011066754 | 6/2011 |
| WO | 2011094423 | 8/2011 |
| WO | 2012068457 | 5/2012 |
| WO | 2012073121 | 6/2012 |
| WO | 2012082493 | 6/2012 |
| WO | WO 2012/082677 | 6/2012 |
| WO | 2012088598 | 7/2012 |
| WO | 2012009506 | 8/2012 |
| WO | 2012102769 | 8/2012 |
| WO | 2012108894 | 8/2012 |
| WO | 2012109506 | 8/2012 |
| WO | 2012109585 | 8/2012 |
| WO | WO 2012/103074 | 8/2012 |
| WO | 2012125991 | 9/2012 |
| WO | 2012166163 | 12/2012 |
| WO | 2012166164 | 12/2012 |
| WO | 2012177727 | 12/2012 |
| WO | 2013036366 | 3/2013 |
| WO | 2013036768 | 3/2013 |

OTHER PUBLICATIONS

Entire patent prosecution history of U.S. Appl. No. 13/276,649, filed, Oct. 19, 2011, entitled, "Stevia Blends Containing Rebaudioside B."

Entire patent prosecution history of U.S. Appl. No. 13/355,852, filed, Jan. 23, 2012, entitled, "Rebaudioside-Mogroside V Blends."

Entire patent prosecution history of U.S. Appl. No. 14/215,647, filed, Mar. 17, 2014, entitled, "Purification of Luo Han Guo Extract."

Gelski, Jeff, "Sweetner Combines Stevia, Luo Han Guo Fruit", FoodBusinessNews.net (Jun. 13, 2011), 1 pg.

International Search Report dated Sep. 27, 2012, Int'l Appl. No. PCT/US2012/022339.

Kinghorn et al., Studies to Identify, Isolate, Develop and Test Naturally Occurring Noncariogenic Sweeteners that May be used as Dietary Sucrose Substitutes, Comprehensive Technical Report for the Period Jun. 25, 1980-Sep. 24, 1983, 35 pages.

Kohda et al., "New Sweet Diterpene Glucosides from Stevia Rebaudiana," Phytochemistry, 1976, pp. 981-983, vol. 14.

Mizukami et al., "Enzymatic Determination of Stevioside in Stevia Rebaudiana," Phytochemistry, 1982, pp. 1927-1930, vol. 21, No. 8.

Mosciano, Gerard, "Developing a Common Language Between Flavorists and Product Developers", Perfumer & Flavorist, vol. 25, (Mar./Apr. 2000) 6 pgs.

Notification of International Preliminary Report on Patentability and Written Opinion issued for PCT/US2012/022339 on Jul. 30, 2013.

Partial International Search Report dated Jun. 22, 2012 for PCT/US2012/022339.

Schiffman, S. S., "Investigation of Synergism in Binary Mixtures of Sweeteners", Brain Research Bulletin, vol. 38, No. 2, (Jan. 20, 1995), 105-120.

Schiffman, Susan S., "Synergism among Ternary Mixtures of Fourteen Sweeteners", Chem. Senses 25, (2000) 131-140.

Yugiang et al. "Production of B-fructofuranosidase and Optimization of Enzymatic Modification Process for Stevioside and Rebaudioside A," Food and Fermentation, vol. 35, issue 03, pp. 23-27, Dec. 21, 2009: Abstract Only.

Chinese Office Action mailed Dec. 24, 2014 in related Application No. 201280010780.7.

Australian Examination Report dated Mar. 17, 2015 for Australian Application No. 2012209241.

Japanese Informative Statement mailed Jan. 30, 2015 in Japanese Application No. 2013-551285.

Translation of Japanese Office Action mailed May 12, 2015 in Japanese Application No. 2013-551961.

Japanese Notice of Reasons for Rejection mailed Jun. 30, 2015 for Japanese Application No. 2013-551285, including English translation.

Office Action mailed Jun. 10, 2015 in U.S. Appl. No. 13/276,649.

Chinese Office Action mailed May 21, 2015 in Chinese Application No. 201180069627.7, including partial translation.

Final Office Action mailed Jul. 22, 2015 in U.S. Appl. No. 13/276,649.

Annex to the European Search Report mailed Oct. 13, 2015 in European Application No. 15177709.1.

Decision of Final Rejection mailed Dec. 1, 2015 for Japanese Application No. 2013-551961.

Notice of Decision of Rejection dated Dec. 2, 2015 for Chinese Application No. 201180069627.7.

Australian Examination Report dated Feb. 2, 2016 for Australian Application No. 2013296597.

Tanaka, Osamu, "Improvement of taste of natural sweeteners", Pure & Appl. Chem., vol. 69, No. 4, 1997, pp. 675-683.

Ohtani et al., "Methods to improve the taste of the sweet principles of Stevia rebaudiana", Stevia. The Genus Stevia., CRC Press 2001, pp. 138-159.

(56) References Cited

OTHER PUBLICATIONS

Sharma et al., "Chemistry and in vivo profile of entkaurene glycosides of Stevia rebaudiana Bertoni—An Overview", Natural Product Radiance, vol. 8(2), 2009, pp. 181-189.
Crammer et al., "Progess in the Chemisty and Properties of Rebaudiosides", Development in Sweetners-3, Elsevier Applied Science, London polypeptide, 1987, pp. 45-64.
Kasai et al., "Synthesis of Sweet Diterpene-Glycoside of Leaves of Stevia; rebaudiosides-A, -D, -E and their relating glycosides as well as Relationship between their Sweetness and Chemical Structure", Journal of Chemical Society Japan 1981 (5), pp. 726-735 with translation.
Chinese Office Action dated Jan. 4, 2016 for Chinese Application No. 201380040911.0 with translation.
Non Final Office Action for U.S. Appl. No. 13/276,649, mailed Jun. 17, 2016, 12 pages.
Definition of Consumable from Websters Online Dictionary uploaded Apr. 28, 2016, http://www.webster-dictionary.org/definition/Consumable, 1 page.
Wolwer-Rieck et al., "Investigations on the stability of stevioside and rebaudioside a in soft drinks", J. Agric. Food Chem, 58(23) pp. 12216-12220, Dec. 8, 2010.
Provisional Application for Stevia Blends Containing Rebaudioside B, filed Jan. 28, 2011, 43 pages. 28.
A. Douglas Kinghorn, "Stevia, The Genus Stevia", chapter 1, published 2002, 22 pages.
A Douglas Kinghorn, "Stevia, The Genus Stevia", chapters 4 and 9, 38 pages.
First Notice of Opposition to a European Patent for EP Application No. EP2667732 Apr. 27, 2016 (submitted on behalf of opponent Cargill, Incorporated by Elseviers Myriam), 20 pages.
Second Notice of Opposition to a European Patent for EP Application No. 2667732, Apr. 29, 2016 (submitted on behalf of opponent Dana Kramer by Vossius & Partner), 26 pages.
Chinese Office Action dated Apr. 20, 2016 for Chinese Application No. 201380040911.0 with translation.
Israel Office Action for Israeli Application No. 236910, dated Jan. 3, 2017, 3 pages.

* cited by examiner

SWEETENER COMPOSITIONS CONTAINING MONK FRUIT EXTRACT AND REBAUDIOSIDES A AND B

CROSS-REFERENCE TO RELATED APPLICATION

This application claims priority to U.S. provisional application No. 61/678,273, filed Aug. 1, 2012, and incorporated herein by reference in its entirety for all purposes.

FIELD OF THE INVENTION

The invention pertains to low or non-caloric sweetener compositions based on glycosides derived from natural sources such as *Stevia rebaudiana* ("*Stevia*") and monk fruit (also known as Luo Han Guo), as well as foods and beverages sweetened with such compositions.

BACKGROUND OF THE INVENTION

Natural caloric sweeteners, such as sucrose, glucose, and fructose, possess desirable taste characteristics, but they add to the caloric content of products. Therefore, there is great consumer interest in low or non-caloric sweeteners that are considered as healthier alternatives. Non-caloric natural and synthetic high-potency sweeteners are known, but they most often possess flavor profiles that are not as desirable to consumers as natural caloric sweeteners. Thus, it is desirable to develop improved non-caloric sweeteners that can be substituted for sugar and that have a more desirable taste profile.

The species *Stevia rebaudiana* ("*Stevia*") is the source of certain naturally occurring sweet steviol glycosides. Considerable research and development has been done to evaluate the use of sweet steviol glycosides of *Stevia* as non-caloric sweeteners. Sweet steviol glycosides that may be extracted from *Stevia* include the six rebaudiosides (i.e., rebaudiosides A to F), stevioside (the predominant glycoside in extracts from wild type *Stevia*), steviolbioside, rubusoside, and dulcosides.

Commercial low or non-caloric sweeteners based on Rebaudioside A and other sweet steviol glycosides tend to have bitter and liquorice aftertastes. These characteristics are especially notable at concentrations above about 300 ppm. In food applications, preferred use levels (8-10% sugar equivalence values) are typically about 500 ppm to about 1000 ppm, above the range at which off-tastes are first noticed. Thus a need continues to exist for reduced-, low-, and/or non-caloric sweeteners including sweet steviol glycosides that have taste profiles with reduced or no bitterness, undesirable flavors (e.g., licorice), or sweetness profiles more like natural caloric sweeteners, or combinations of such properties.

The species *Siraitia grosvenorii*, an herbaceous perennial vine native to southern China and Northern Thailand, has also been investigated as a source of intensely sweet glycosides (mogrosides), with the main sweet component being mogroside V. It is one of four species in the genus *Siraitia*. Botanical synonyms include *Momordica grosvenorii* and *Thladiantha grosvenorii*. The fruit of this species, which is commonly referred to as monk fruit or Luo Han Guo, may be subjected to an extraction procedure whereby the resulting extract contains mogroside V and other mogrosides in concentrated, purified form. By itself, monk fruit extract may not have a temporal profile which makes it completely acceptable as a non-caloric replacement for caloric sweeteners (sugars) in food and beverage compositions.

Accordingly, there remains a desire to develop low- and non-caloric sweetener compositions based on naturally obtained glycosides having high sweetness intensity which have improved taste (e.g., less bitterness, lower levels of off-flavors, reduced aftertaste, or any combination of such attributes).

BRIEF SUMMARY OF THE INVENTION

One aspect of the invention provides a sweetener composition comprised of:
 a) monk fruit extract comprising mogroside V;
 b) rebaudioside A; and
 c) rebaudioside B;
 wherein:
 the monk fruit extract, rebaudioside A and rebaudioside B are present in a weight ratio of monk fruit extract:(rebaudioside A+rebaudioside B) of 51:49 to 99:1;
 the mogroside V and rebaudioside A are present in a weight ratio of from 41:59 to 99:1 mogroside V: rebaudioside A; and
 the rebaudioside B is present in an amount effective to improve the taste of the sweetener composition.

Another aspect of the invention provides a sweetener composition comprised of:
 a) monk fruit extract comprising 45 to 55 weight % mogroside V;
 b) rebaudioside A; and
 c) rebaudioside B;
 wherein:
 the monk fruit extract, rebaudioside A and rebaudioside B are present in a weight ratio of monk fruit extract:(rebaudioside A+rebaudioside B) of 55:45 to 80:20;
 the mogroside V and rebaudioside A are present in a weight ratio of from 45:55 to 65:35 mogroside V:rebaudioside A; and
 the rebaudioside B is present in an amount of at least 5 (e.g., 5 to 12) weight %, based on the total weight of a), b), c) and any additional steviol glycosides present (in addition to rebaudioside A and rebaudioside B).

Yet another aspect of the invention provides a sweetener composition comprised of:
 a) 53 to 68 weight % monk fruit extract comprising 45 to 55 weight % mogroside V;
 b) 26 to 35 weight % rebaudioside A; and
 c) 6 to 12 weight % rebaudioside B, wherein a), b) and c) in total equal 100% [i.e., weight % a)+weight % b)+weight % c=100%].

The invention in another aspect provides a food or beverage composition comprising at least one food or beverage ingredient and one of the above-mentioned sweetener compositions. Such food and beverage compositions may be prepared by combining one or more food or beverage ingredients with an amount of one of the above-mentioned sweetener compositions effective to impart a sweeter taste to the one or more food or beverage ingredients.

A method of making a sweetener composition is also provided in another aspect of the invention, wherein the method comprises combining a monk fruit extract with an amount of rebaudioside A and an amount of rebaudioside B effective to improve the sweetness taste quality of the monk fruit extract.

DETAILED DESCRIPTION OF CERTAIN EMBODIMENTS OF THE INVENTION

A monk fruit extract containing mogroside V constitutes one component of the sweetener compositions of the present invention. Methods of obtaining such monk fruit extracts (sometimes referred to as Luo Han Guo extracts) are well known in the art and any of such methods may be utilized in order to prepare the monk fruit extract to be employed in the present sweetener compositions. Suitable preparation methods are described, for example, in US Patent Publication 2011/0021456. Prior to use in the sweetener compositions of the present invention, the monk fruit extract may be subjected to various purification procedures in order to reduce or eliminate off-flavors, off-colors and/or off-tastes that might otherwise be present. Examples of such purification procedures include, without limitation, treatment with activated carbon, treatment with various types of ion exchange resins or other adsorbents, and the like. Typically, the monk fruit extract is in dry, powdered form, but in alternative embodiments the monk fruit extract may be in solution form (e.g., as a concentrated aqueous solution or syrup). It will generally be desirable to employ a monk fruit extract having a relatively high mogroside V content, e.g., at least 20, at least 25, at least 30, at least 35, at least 40 or at least 45 weight % mogroside V (on a dry solids basis). The monk fruit extract may be essentially pure (i.e., at least 95 weight % pure) mogroside V, but because the cost of producing high purity mogroside V may be excessive from a commercial point of view typically it will be economically advantageous to use a monk fruit extract containing not more than 95, not more than 90, not more than 85, not more than 80, not more than 75, not more than 70 or not more than 65 weight % mogroside V (on a dry solids basis). For example, the monk fruit extract may have a mogroside V content of 45 to 55 weight %. In addition to the mogroside V, the monk fruit extract may contain other constituents, in particular other terpene glycosides such as mogroside II-IV and VI, 11-oxo-mogroside V, grosmomoside I, and siamenoside I as well as protein fragments, melanoidins and flavonoids.

In various embodiments of the invention, the sweetener composition may be comprised of at least 45, at least 51, at least 53, or at least 55 weight percent (on a dry solids basis) monk fruit extract.

Monk fruit extracts available from commercial sources may be used in the present invention. For example, the monk fruit extracts sold under the brand names PUREFRUIT (by Tate & Lyle) and FRUIT-SWEETNESS (by BioVittoria) are generally suitable for use.

Rebaudioside A is one of the constituents of *Stevia* and may be isolated from *Stevia* extracts using known techniques. Rebaudioside A is also available in purified form from various commercial sources. The rebaudioside A component of the sweetener composition of the present invention may be introduced into the composition in pure or essentially pure (i.e., at least 95 weight % pure) form or in admixture with other constituents, provided such other constituents do not detract from the taste quality and other attributes of the sweetener composition to an unacceptable degree.

The rebaudioside B component of the present sweetener compositions can be obtained in various ways. For example, rebaudioside B can be isolated from plant extracts by chromatography, precipitation, and/or crystallization. Rebaudioside B may also be prepared by treating rebaudioside A with various hydroxides of mono, di, and trivalent cations under appropriate temperature and pH conditions. The conversion to rebaudioside B may be carried out to completion or near completion and essentially pure rebaudioside B isolated by chromatography, precipitation, selective crystallization or other such purification technique. Alternatively, less than 100% of the rebaudioside B is converted and the resulting rebaudioside A/rebaudioside B mixture used as a source of both the rebaudioside A and rebaudioside B components of the sweetener composition of the present invention (or at least a portion of such components, with the balance being supplied from other sources). Rebaudioside B can also be obtained in a similar manner by treating rebaudioside D with the same hydroxide-containing compounds mentioned above in connection with the conversion of rebaudioside A to rebaudioside B. Rebaudioside B can also be produced enzymatically from rebaudioside A or D. Such methods for producing rebaudioside B are all known in the art. Rebaudioside B is also available from various commercial sources. The rebaudioside B to be combined with the other components of the sweetener composition may be essentially pure (e.g., at least 95 weight % pure) or be supplied as an admixture with other constituents (e.g., rebaudioside A) provided such other constituents do not detrimentally affect the taste quality of the sweetener composition to an unacceptable extent.

In various embodiments of the invention, the sweetener composition may be comprised of at least 5, at least 10, at least 15, at least 20, or at least 25 weight percent (on a dry solids basis) rebaudioside A. In other embodiments, the sweetener composition does not contain more than 45, not more than 40, or not more than 35 weight percent (on a dry solids basis) rebaudioside A. The aforementioned weight percentages are based on the total weight of monk fruit extract, rebaudioside A and rebaudioside B.

In the sweetener composition of the present invention, mogroside V and rebaudioside A may be present in a weight ratio of from 41:59 to 99:1 mogroside V: rebaudioside A. In other embodiments of the invention, such weight ratio may be within any of the following ranges: 41:59 to 85:15; 41:59 to 75:25; or 45:55 to 65:35.

The monk fruit extract, rebaudioside A and rebaudioside B components of the sweetener composition may be present in amounts such that the weight ratio of monk fruit extract: (rebaudioside A+rebaudioside B) is in the range of 51:49 to 99:1. In other embodiments of the invention, such weight ratio may be within any of the following ranges: 51:49 to 90:10; 55:45 to 80:20; or 60:40 to 75:25.

It has been unexpectedly discovered that the addition of rebaudioside B to a sweetener composition containing monk fruit extract and rebaudioside A helps to improve the taste of the sweetener composition as compared to the taste of an analogous composition that does not contain any rebaudioside B. That is, for reasons not fully understood, the presence of rebaudioside B in such a composition serves to enhance the acceptability of the composition as a sweetener and in particular tends to reduce the perceived bitterness of the composition. Thus, in one embodiment, an amount of rebaudioside B is present in combination with a composition comprised of monk fruit extract and rebaudioside A which is effective to improve the taste of the composition. The threshold amount of rebaudioside B needed to achieve a perceived improvement in taste will vary somewhat depending upon the form in which the composition is consumed (e.g., whether the sweetener composition is consumed as a food or beverage, with the threshold amount also being dependent upon the identity and nature of other ingredients of the food or beverage) and is also somewhat subjective (since individuals may have different perceptions or preferences with respect to sweetened compositions). Where the composition contains stevioside, in addition to the monk fruit extract and rebaudioside A, somewhat more rebaudioside B may be needed to achieve the desired level of taste improvement as compared to the amount of rebaudioside B needed to impart a comparable taste acceptability to an analogous composition which does not contain stevioside. However, typically at least 1, 2, 3, 4 or 5 weight % rebaudioside B (expressed on a dry solids basis and calculated as a percentage of the total weight of monk fruit extract, rebaudioside A, rebaudioside B and any steviol glycosides other than rebaudioside A and rebaudioside B, such as stevioside) is present in the sweetener composition of the present invention. In certain embodiments, the amount of rebaudioside B does not exceed 20, 18, 16, 14 or 12 weight % (on a dry solids basis and calculated as a percentage of the total weight of monk fruit extract, rebaudioside A, rebaudioside B and any steviol glycosides other than rebaudioside A and rebaudioside B). Thus, in various exemplary embodiments of the invention the rebaudioside B content of the sweetener composition is 5 to 15 weight % or 6 to 12 weight % (on a dry solids basis and calculated as a percentage of the total weight of monk fruit extract, rebaudioside A, rebaudioside B and any steviol glycosides other than rebaudioside A and rebaudioside B).

In one aspect of the invention, the sweetener composition contains little or no stevioside (e.g., less than 20, less than 15, less than 10, or less than 5 weight % stevioside, on a dry solids basis and calculated as a percentage of the total weight of monk fruit extract, rebaudioside A, rebaudioside B and any steviol glycosides other than rebaudioside A and rebaudioside B).

Sweetener compositions in accordance with the invention may be processed using known methods to modify particle size and physical form. Methods such as agglomeration, grinding, milling, compaction, screening, sieving, spray-drying, drum drying and other forms of physical processing may be applied to adjust particle size or other attributes of the composition in order to deliver better flow, hydration, dissolution or other properties. The sweetener composition may be in solid form, such as a powder, granules, beads, tablets, or the like. The sweetener composition may also be provided in liquid forms, such as aqueous solutions, syrups or emulsions, optionally containing one or more preservatives and/or processing aids, for ease of use in specific applications. The sweetener compositions of the present invention may be co-processed with bulking agents such as a bulk sweetener, a lower glycemic carbohydrate, a fiber, a hydrocolloid and the like or combinations thereof to deliver products with controlled sweetness, dosing, potency and handling properties.

The sweetener composition of the present invention may be incorporated into any type of food or beverage composition. Non-limiting examples of such food and beverage compositions include baked goods, soups, sauces, processed meats, canned fruits, canned vegetables, dairy products, frozen confections, carbonated soft drinks, sports drinks, ready to drink teas, dairy drinks, alcoholic beverages, energy drinks, flavored waters, vitamin drinks, fruit drinks, fruit juices, powdered soft drinks, candy, confections, chewing gum, nutraceutical products and the like. The sweetener composition may also be used in products such as medicines, pharmaceutical products and tobacco products.

Thus, the sweetener composition of the present invention may, for example, be utilized as an ingredient or component of a product, wherein the product is a food product, a beverage product, a pharmaceutical product, a nutraceutical product, a sports product, a tobacco product or a cosmetic product.

Illustrative, non-limiting examples of food products comprising a sweetener composition in accordance with the present invention may be selected from the group consisting of confectionary products, dessert products, cereal products, baked goods, frozen dairy products, meats, dairy products, condiments, snack bars, soups, dressings, mixes, prepared foods, baby foods, diet preparations, syrups, food coatings, dried fruits, sauces, gravies, jams/jellies, spreads, batters, breadings, spice mixes, frostings, and coatings.

Illustrative, non-limiting examples of beverage products comprising a sweetener composition in accordance with the present invention may be selected from the group consisting of concentrated beverage mixes, carbonated beverages, non-carbonated beverages, fruit-flavored beverages, fruit-juices, teas, milk, coffees, nectars, powdered soft drinks, liquid concentrates, milk drinks, smoothies, alcoholic beverages, flavored waters and combinations thereof.

The sweetener composition is included in an amount effective to impart the desired amount of sweetness to the sweetened product. The product may contain one or more additional sweeteners, e.g., a caloric sweetener such as sugar or another high intensity sweetener (either natural or synthetic) or may be free of any sweetening component other than the sweetener composition of the present invention. The sweetener compositions described herein may also find utility as taste enhancers, wherein they are included in a food or beverage at a concentration below the threshold where they impart a sweet taste to the product but in sufficient amount that they improve, modify or enhance the taste of the product.

In some embodiments, the sweetener composition of the invention is present in the foodstuff or beverage at a concentration of at least 50, at least 200, at least 500, at least 1000, at least 1500 or at least 2000 ppm (based on weight).

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

Sweetener Blends 1-3 were prepared by incorporating different levels of rebaudioside B (80% purity, containing a minor amount of rebaudioside A) into mixtures of a monk fruit extract and a *Stevia* product, where the monk fruit extract and *Stevia* product are blended in various proportions. The monk fruit extract was PUREFRUIT™ Select, available from Tate & Lyle, which contained 50 weight % mogroside V. The *Stevia* product was a commercially available product containing approximately 71 weight % rebaudioside A and 25 weight stevioside. The mogroside V, rebaudioside A, stevioside and rebaudioside B content (in weight %) of each of Sweetener Blends 1-3 is shown in the following Table 1.

TABLE 1

| Blend | Monk Fruit Extract:Stevia Product:Reb B | Mogroside V | Rebaudioside A | Stevioside | Rebaudioside B |
|---|---|---|---|---|---|
| 1 | 52:36:12 | 26 | 26.0 | 9 | 9.6 |
| 2 | 60:30:10 | 30 | 21.7 | 7.5 | 8 |
| 3 | 68:24:8 | 34 | 17.3 | 6 | 6.4 |

Sweetener Blends 1-3 were compared to PUREFRUIT™ Plus, sold by Tate & Lyle, by expert tasters for sweetness intensity, bitterness, and overall acceptability. PUREFRUIT™ Plus is a blend of high potency sweeteners derived from extracts of monk fruit and *Stevia*, containing monk fruit extract, rebaudioside A, stevioside and other steviol glycosides, but no rebaudioside B.

The results obtained, which are shown in the following Table 2, demonstrated that Sweetener Blends 1 and 2 were less bitter and more acceptable than the PUREFRUIT™ Plus control, which did not contain any rebaudioside B. The scores given are the average for the expert panelists, who ranked the samples for each attribute with 1="least" and 4="most".

TABLE 2

| Blend | Sweetness Intensity | Bitterness | Overall Acceptability |
|---|---|---|---|
| PUREFRUIT™ Plus (Control) | 1.8 | 2.8 | 2 |
| 1 | 3.2 | 2 | 3.4 |
| 2 | 3 | 2.2 | 3.2 |
| 3 | 2 | 3 | 1.4 |

Example 2

Sweetener Blend 4 was prepared by combining 75 parts by weight of PUREFRUIT™ Select [a Luo Han Guo (monk fruit) extract commercially available from Tate & Lyle containing 50 weight % mogroside V, the balance being predominantly other mogrosides], 19.5 parts by weight rebaudioside A, and 5.5 parts by weight rebaudioside B. Sweetener Blend 4 contained 37.5 weight % mogroside V, 19.5 weight % rebaudioside A, and 5.5 weight % rebaudioside B. Thus, the weight ratio of rebaudioside A to rebaudioside B was 78:22, the weight ratio of mogroside V to rebaudioside A was 65.8:34.2, the weight ratio of monk fruit extract:(rebaudioside A+rebaudioside B) was 75:25, and the weight ratio of mogroside V to rebaudioside B was 87.2:12.8.

Sweetener Blend 5 was prepared by combining 60 parts by weight PUREFRUIT™ Select, 31.2 parts by weight rebaudioside A, and 8.8 parts by weight rebaudioside B. Thus, Sweetener Blend 5 contained 30 weight % mogroside V, 31.2 weight % rebaudioside A, and 8.8 weight % rebaudioside B. Accordingly, the weight ratio of rebaudioside A to rebaudioside B was 78:22, the weight ratio of mogroside V to rebaudioside A was 49:51, the weight ratio of monk fruit extract:(rebaudioside A+rebaudioside B) was 60:40, and the weight ratio of mogroside V to rebaudioside B was 77.3:22.7.

The taste of each of Sweetener Blend 4 and 5 was compared by expert tasters to the taste of PUREFRUIT™ Plus, as described in Table 3.

TABLE 3

| Sweetener | Sweetness Scores | Sweetness, Ave. | Preference, Scores | Preference, Ave. |
|---|---|---|---|---|
| Blend 4 | 3, 3, 2, 3 | 2.75 | 1, 3, 2, 2 | 2 |
| Blend 5 | 2, 2, 3, 1 | 2 | 2, 2, 3, 3 | 2.5 |
| PUREFRUIT™ Plus | 1, 1, 1, 2 | 1.25 | 3, 1, 1, 1 | 1.5 |

The results from this assessment indicated that the taste of Sweetener Blend 5 was significantly preferred over that of PUREFRUIT™ Plus, with the taste of Sweetener Blend 4 being somewhat preferred over that of PUREFRUIT™ Plus. This result was unexpected as previous evaluations of sweeteners based on blends of monk fruit extracts and *Stevia* extracts had indicated that sweetener compositions comprising mogroside V and a rebaudioside component with weight ratios of between 1:1 and 6:1 mogroside V:rebaudioside provided the best sweetness quality. Additional testing showed that Sweetener Blend 5 was significantly preferred as a sweetener over PUREFRUIT™ Plus in various beverage compositions.

Sweetener Blend 5 was further evaluated in a lemon lime carbonated soft drink and tested for preference against a corresponding product sweetened only with rebaudioside A. The results obtained showed that Sweetener Blend 5 was preferred over the rebaudioside A-sweetened formulation by 65% of the panelists. In contrast, a similar product sweetened with a 78:22 blend of rebaudioside A and rebaudioside B was preferred by only 55% of the panelists, as compared to the rebaudioside A-sweetened formulation.

What is claimed is:
1. A sweetener composition comprising:
a) 53 to 68 weight % monk fruit extract comprising 45 to 55 weight % mogroside V, both on a dry weight basis;
b) 26 to 35 weight % rebaudioside A on a dry weight basis;
c) rebaudioside B; and
d) optionally, additional steviol glycosides;
wherein:
the monk fruit extract, rebaudioside A and rebaudioside B are present in a weight ratio of monk fruit extract:(rebaudioside A+rebaudioside B) of 55:45 to 80:20 on a dry weight basis;
the mogroside V and rebaudioside A are present in a weight ratio of from 45:55 to 65:35 mogroside V:rebaudioside A;
the rebaudioside A and rebaudioside B are present in a weight ratio of 65:35 to 90:10 rebaudioside A:rebaudioside B; and
the rebaudioside B is present in an amount of 6 to 12 weight %, based on the total weight of a), b), c), and d) on a dry weight basis, wherein a), b), c), and d) total to 100%;

wherein the rebaudioside B improves the taste of the sweetener composition as compared to an analogous sweetener composition that does not contain rebaudioside B.

2. The sweetener composition of claim 1, wherein the weight ratio of monk fruit extract:(rebaudioside A+rebaudioside B) is from 60:40 to 75:25.

3. The sweetener composition of claim 1, wherein rebaudioside A and rebaudioside B are present in a weight ratio of 70:30 to 85:15 rebaudioside A: rebaudioside B.

4. The sweetener composition of claim 1, wherein the sweetener composition comprises 0 to 10 weight % stevioside, based on the total weight of a), b), c), and d).

5. A sweetener composition comprising:
   a) monk fruit extract comprising 45 to 55 weight % mogroside V on a dry weight basis;
   b) rebaudioside A;
   c) rebaudioside B; and
   d) optionally, additional steviol glycosides;
wherein:
   the monk fruit extract, rebaudioside A and rebaudioside B are present in a weight ratio of monk fruit extract:(rebaudioside A+rebaudioside B) of 55:45 to 80:20 on a dry weight basis;
   the mogroside V and rebaudioside A are present in a weight ratio of from 45:55 to 65:35 mogroside V:rebaudioside A;
   the rebaudioside A and rebaudioside B are present in a weight ratio of 65:35 to 90:10 rebaudioside A:rebaudioside B; and
   the rebaudioside B is present in an amount of at least 6 weight % based on the total weight of a), b), c), and d) on a dry weight basis, wherein a), b), c), and d) total to 100%;
wherein the rebaudioside B improves the taste of the sweetener composition as compared to an analogous sweetener composition that does not contain rebaudioside B.

6. A sweetener composition comprising:
   a) 55 to 68 weight % monk fruit extract comprising 45 to 55 weight % mogroside V, both ranges being on a dry weight basis;
   b) 26 to 35 weight % rebaudioside A on a dry weight basis; and
   c) 6 to 12 weight % rebaudioside B on a dry weight basis;
wherein a), b) and c) are 100% in total.

7. A food or beverage composition comprising at least one food or beverage ingredient and a sweetener composition in accordance with claim 1.

8. A food or beverage composition comprising at least one food or beverage ingredient and a sweetener composition in accordance with claim 5.

9. A food or beverage composition comprising at least one food or beverage ingredient and a sweetener composition in accordance with claim 6.

10. The sweetener composition of claim 5, wherein the rebaudioside B is present in an amount of 6 to 12 weight %, based on the total weight of a), b), c) and any additional steviol glycosides present.

11. The sweetener composition of claim 5, wherein the sweetener composition comprises 0 to 10 weight % stevioside, based on the total weight of a), b), c), and d).

* * * * *